United States Patent [19]

Baker et al.

[11] Patent Number: 5,600,051
[45] Date of Patent: Feb. 4, 1997

[54] ENHANCING OLEFIN YIELD FROM CRACKING

[75] Inventors: R. Terence K. Baker; Nelly M. Rodriguez, both of State College, Pa.

[73] Assignee: Corning Incorporated, Corning, N.Y.

[21] Appl. No.: 445,319

[22] Filed: May 19, 1995

[51] Int. Cl.$^6$ ...................................................... C07C 4/04
[52] U.S. Cl. ........................... 585/648; 585/649; 585/650; 585/651; 585/652; 585/653; 585/920; 208/132
[58] Field of Search ..................... 585/648, 649, 585/650, 651, 652, 653, 920, 950; 208/48 R, 132

[56] References Cited

U.S. PATENT DOCUMENTS

| | | | |
|---|---|---|---|
| 3,329,735 | 7/1967 | Paul et al. | 585/652 |
| 3,536,776 | 10/1970 | Lo | 208/48 R |
| 3,597,241 | 8/1971 | Perugini | 75/252 |
| 3,644,557 | 2/1972 | Senes et al. | 585/651 |
| 3,827,967 | 8/1974 | Nap et al. | 585/653 |
| 4,379,745 | 4/1983 | Polizzotti et al. | 208/132 |
| 5,250,360 | 10/1993 | Andrus et al. | 428/471 |
| 5,298,332 | 3/1994 | Andrus et al. | 428/469 |

FOREIGN PATENT DOCUMENTS 1199483  7/1970  United Kingdom .

*Primary Examiner*—Glenn A. Caldarola
*Assistant Examiner*—Walter D. Griffin
*Attorney, Agent, or Firm*—Milton M. Peterson

[57] ABSTRACT

An improved method of thermally cracking hydrocarbons to produce olefin wherein a gaseous stream containing hydrocarbons is passed through a heated metal tube in a pyrolysis furnace, the improvement comprising enhancing the olefin yield by exposing the gaseous stream to a barium silicate glass-ceramic as the gaseous stream passes through the tube.

9 Claims, 2 Drawing Sheets

5,600,051

ENHANCING OLEFIN YIELD FROM CRACKING

RELATED APPLICATIONS

Pending U.S. applications Ser. No. 08/427,338 entitled THERMAL CRACKING PROCESS AND FURNACE ELEMENTS and Ser. No. 08/427,381 entitled METHOD OF PROTECTING METAL were filed on Apr. 24, 1995 and assigned to the same assignee as the present application.

The former is directed to lessening the tendency for carbon to deposit on a metal surface when the surface is exposed, while heated, to a gaseous stream containing hydrocarbons. It is further directed to a thermal cracking process for olefin production and to furnace elements for use in a thermal cracking furnace that are provided with a glass-ceramic coating.

The latter is directed to protecting a metal from embrittlement due to carburization. The metal is insulated from contact with carbon by a glass-ceramic coating on the exposed metal surface.

FIELD OF THE INVENTION

Enhancing the olefin yield by catalytic action during thermal cracking of hydrocarbons is the field of the invention.

BACKGROUND OF THE INVENTION

The invention is concerned with thermal cracking of hydrocarbons to produce olefins. It is particularly concerned with a catalytic method of enhancing the yield of olefins from the process.

Thermal cracking is a process wherein a hydrocarbon is converted to a new form by the influence of heat. The present invention is concerned with such a process used for olefin production.

The process is carried out in a cracking furnace that comprises a fire box enclosing a serpentine array of tubing. The array comprises a plurality of interconnected tubes and fittings totalling several hundred meters in length. The tubing array is maintained at a carefully controlled temperature, usually at least 750° C., while the furnace is in operation.

The process involves passing a gaseous stream containing the feedstock through the heated tubing under pressure and at a high velocity. The resulting product is quenched as it exits the furnace, and is collected for further processing.

In converting hydrocarbons, it is customary to mix the hydrocarbons with steam as a diluent. The presence of steam enhances the yield, presumably because it prevents side reactions which partially consume the desired end product. It would be desirable to further enhance the yield, and it is a purpose of the present invention to provide such enhancement.

It has long been known that the presence of specific barium compounds serves to catalyze a wide variety of organic chemical reactions. In particular, a thermal cracking process has been described in which a hydrocarbon is mixed with hot combustion gases containing a finely divided metal oxide. A number of oxides are given as examples, barium oxide being one of the oxides listed.

For whatever reason, such catalytic efforts to enhance olefin output, except for the use of steam, have not found commercial favor. One need, of course, is to provide an inexpensive, convenient method of providing effective contact between the catalyst and the feedstock. Another need is to avoid contaminating the product and/or requiring an expensive means of separation. The present invention meets these needs.

SUMMARY OF THE INVENTION

An improved method of thermally cracking hydrocarbons to produce olefins wherein a gaseous stream containing hydrocarbons is passed through a heated metal tube, in a pyrolysis furnace, the improvement comprising enhancing the olefin yield by exposing the gaseous stream to the surface of a barium silicate glass-ceramic as the gaseous stream passes through the tube.

PRIOR ART

Literature of possible interest is listed on an attached document.

DESCRIPTION OF THE INVENTION

The invention arose in the course of experimental work undertaken to investigate the effectiveness of glass-ceramic coatings as anti-coking agents in accordance with a related application. An anti-coking agent lessens carbon deposition on the interior wall of a pyrolitic furnace during the cracking of hydrocarbons.

A number of different glass-ceramic materials were treated to determine anticoking characteristics. At the same time, the yield of ethylene and other products was measured for each sample as a control. Each of the samples tested showed a capability to inhibit coking.

Quite unexpectedly, it was observed that the ethylene output was appreciably enhanced with one sample. Meanwhile, the other samples showed no unusual effect on the yield of ethylene. The glass-ceramic in the sample exhibiting a catalytic effect had a composition containing only oxides of barium, aluminum and silicon.

Figure 1:
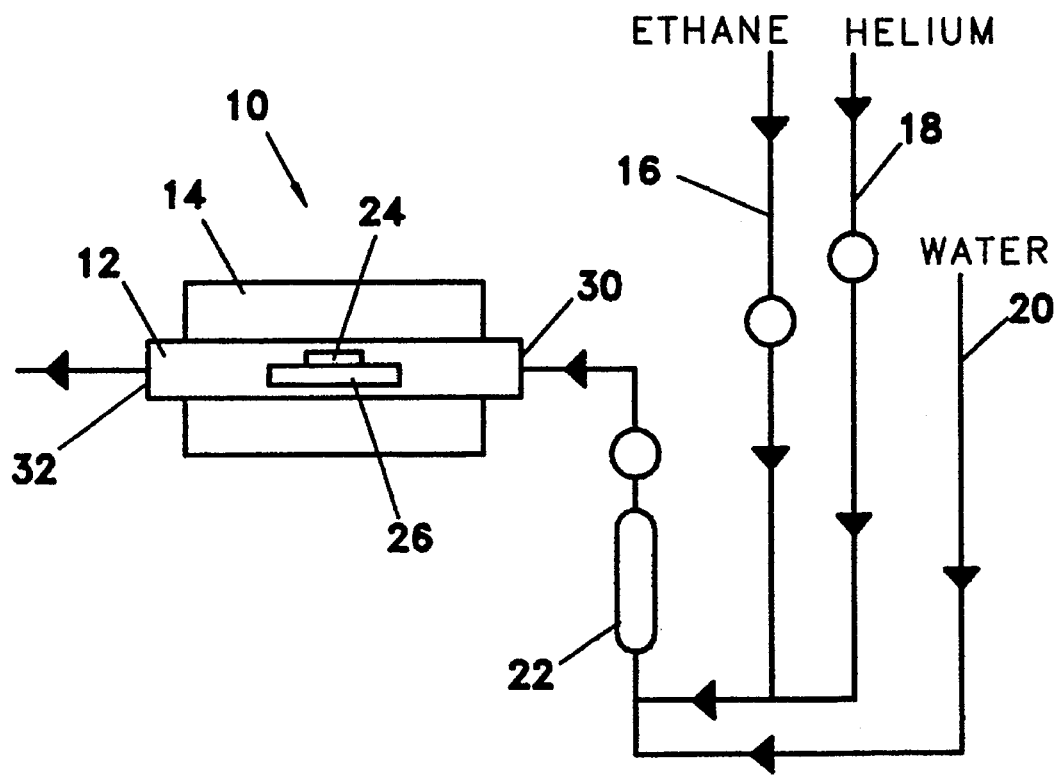
FIG. 1 is a schematic representation of an apparatus employed in experimental practice of the invention.

FIG. 1 is a schematic representation of an apparatus generally designated that was employed in the experimental testing that led to the invention. Glass-ceramics were tested in the form of solid bodies inserted in a reactor tube as test pieces.

Figure 2:
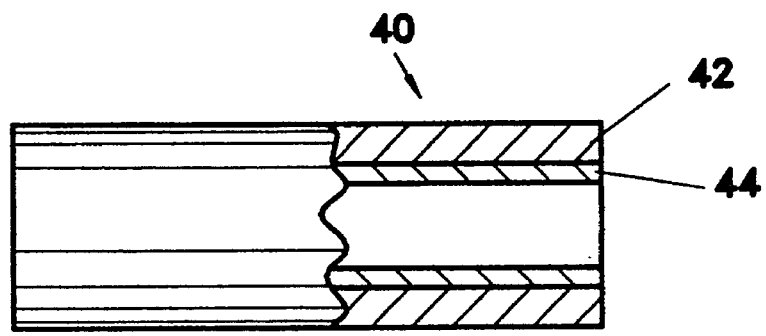
FIG. 2 is a front elevation view, partly broken away, showing a segment of a reactor tube used in practicing the invention in a commercial furnace.

FIG. 2 is a front elevation view, partly broken away, of a segment of a commercial reactor tube 40 illustrating use of the invention. Reactor tube 40 comprises a cast alloy tube 42 having a glass-ceramic sleeve 44 designed to have its surface 46 exposed to a gaseous stream passing through tube 40. Sleeve 44 will have a predominant crystal phase of a barium silicate.

Apparatus 10 comprises a quartz reactor tube 12 positioned in an electrically heated furnace 14. A feedstock stream was provided to reactor tube 12 by mixing ethane from a source 16 with a carrier gas, helium, from a source 18 and water from a source 20. Each source was provided with valves and controllers (not shown). The mixture was passed through a steam generator 22 to generate a gaseous mixture that was discharged into reactor tube 12.

In carrying out a test, a test sample 24 was placed on a quartz holder 26 and inserted in heated tube 12. Reactor tube 12 was a quartz tube 90 cm in length and 4 cm in diameter. It was positioned in furnace 16, and was provided with a sealed entry 30 and a sealed exit 32.

Furnace 14 was designed to heat samples to temperatures in the range of 600°–900° C. With the furnace at temperature and a sample in place, a mixture of ethane and steam, in a 4:1 volume ratio, was introduced into tube 12 at entry 30.

Samples of the gaseous product were withdrawn at regular intervals at exit 32. The samples were analyzed by gas chromatography using a Varian 3500 unit equipped with a megabore column. At the completion of each reaction, the sample was cooled to room temperature.

Initial studies were conducted at 850° C. for periods of time ranging up to 13 hours. The studies were designed to determine the time required to obtain an amount of carbon deposition sufficient for measurement. Accordingly, tests were made on 5 cm (2") long coupons of an Fe—Cr—Ni alloy containing 0.45% carbon (HP-45 alloy). The coupons were cut from a cracking furnace tube and tested in a bare, or exposed, metal state.

It was determined that progressively increasing amounts of carbon were deposited with time, but that the rate was slower above 7 hours. Accordingly, comparative material runs were made for a period of 7 hours with the furnace temperature at 850° C.

A comparative rest was then made on a glass-ceramic coupon under similar conditions. These conditions were exposure for 7 hours at 850° C. to a steady flow of ethane and steam in a 4:1 volume ratio. This initial test on a glass-ceramic material clearly indicated that suppression of carbon deposition occurred. However, there was also an indication that a catalytic effect on ethane decomposition might be occurring.

This led to comparative testing of five different glass-ceramic materials provided in the form of coupons. During each test, the exiting gas stream was sampled and rested for percentage yield of each material in the stream. Also, carbon deposition was determined by weight difference of the sample. Yields of methane, ethane and ethylene were calculated as moles of each product divided by the moles of ethane in the incoming stream.

TABLE 1 shows the compositions of five glass-ceramic bodies that were tested. The compositions are shown in percent by weight as calculated on an oxide basis. Also shown are the percent ethylene determinations made on the outlet stream as described above.

TABLE 1

|  | 1 | 2 | 3 | 4 | 5 |
| --- | --- | --- | --- | --- | --- |
| $SiO_2$ | 9.6 | 32.0 | 65.0 | 54.1 | 62.7 |
| $Al_2O_3$ | 32.5 | — | 6.9 | 5.7 | 5.3 |
| $B_2O_3$ | 22.2 | — | — | — | — |
| BaO | — | 40.9 | — | — | 32.0 |
| CaO | 35.8 | — | — | — | — |
| $ZrO_2$ | — | 8.2 | — | — | — |
| MnO | — | 18.9 | — | — | — |
| SrO | — | — | 28.1 | 23.3 | — |
| NiO | — | — | — | 16.8 | — |
| % yield | 25% | 26% | 25% | 28% | 38% |

For comparison purposes, a test run with a bare metal sample showed 27% ethylene; a test run with no sample in the tube showed 25% ethylene. It is apparent that only the test with composition 5 deviated appreciably in yield of ethylene. This indicates that only a glass-ceramic containing a predominant barium silicate crystal phase is effective in enhancing the yield of ethylene in a thermal cracking process. However, each of the five glass-ceramics was essentially equally effective in reducing carbon deposition during the test run.

Figure 3:
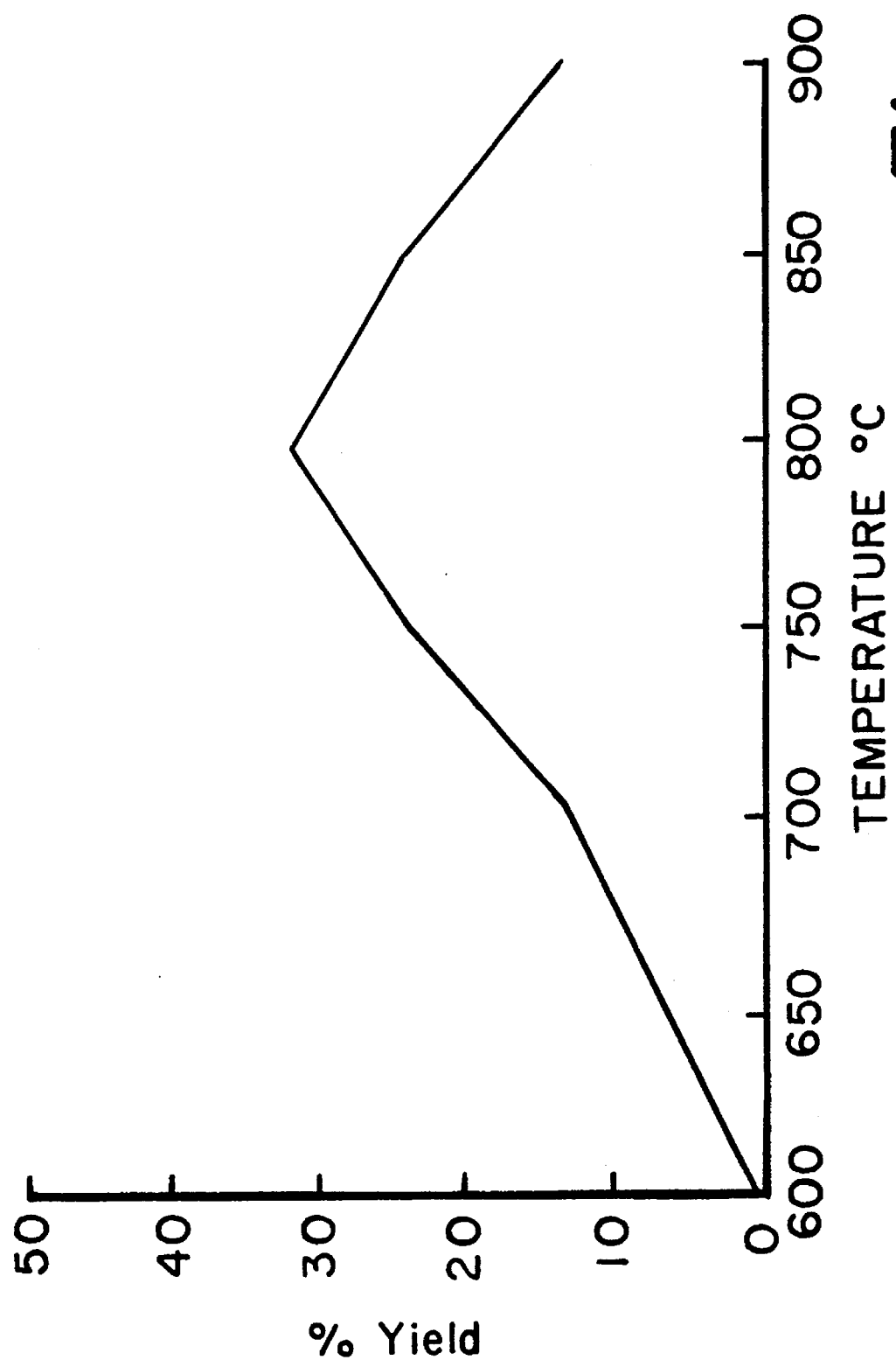
FIG. 3 is a graphical representation of ethylene yield variation with temperature.

Blank runs, that is, without any test pieces in the equipment, were made to determine the effect of temperature on ethylene production in the basic process. These runs were of two hours duration, and were carried out at spaced intervals over the temperature range of 600°–900° C. employing the test equipment of FIG. 1. FIG. 3 displays graphically the ethylene yields measured during the blank runs at the different temperatures. In FIG. 3, % yield is plotted on the vertical axis and temperature in ° C. on the horizontal axis. As the graph indicates, ethylene yield increased at temperatures up to about 800° C. and then declined at higher temperatures. Accordingly, further testing was conducted at about 800° C.

Two further test runs were then made under identical conditions. These runs were made to determine whether the apparent catalytic effect of the barium aluminosilicate glass-ceramic could be confirmed. The test apparatus shown in FIG. 1 was operated with an essentially constant flow of ethane and steam at a 4:1 volume ratio. Each test was conducted for five hours at 800° C.

One test run employed a coupon of the glass-ceramic shown as Example 5 of TABLE I. The other run employed a quartz coupon as a standard for comparison. The output was sampled at eight spaced intervals over each five hour run. The output remained relatively consistent throughout each run.

Both runs showed a rather higher yield of ethylene at 800° C. than the outputs measured at 850° C. in the initial runs comparing the glass-ceramics and standards. This would be predicted based on the showing of temperature effect on yield in blank runs as shown in FIG. 3. The earlier runs, of course, were made at 850° C. The run with the quartz standard at 800° C. showed an output of about 38% throughout the run. The run with the glass-ceramic at 800° C. showed an ethylene output of about 50%. This 12% increase in yield in the presence of the glass-ceramic of Example 5, as compared to the quartz standard, is consistent with the increase in yield observed in the initial runs comparing this example with a standard. The difference in the actual percentage yields, as noted above, was occasioned by the difference in run temperatures as predicted from the data displayed in FIG. 3. The 12% increase in yield confirms the catalytic effect of exposure to a barium aluminosilicate glass-ceramic on ethylene yield in a thermal cracking process.

I claim:

1. In a method of thermally cracking hydrocarbons to produce olefins wherein a gaseous stream containing hydrocarbons is passed through a heated metal tube in a pyrolysis/furnace, the improvement comprising enhancing the olefin yield by exposing the gaseous stream containing hydrocarbons to the surface of a barium silicate glass-ceramic as the gaseous stream passes through the tube.

2. A method in accordance with claim 1 which comprises passing a gaseous stream composed essentially of at least one hydrocarbon, steam and a carrier gas over the glass-ceramic surface.

3. A method in accordance with claim I which comprises passing a gaseous stream containing ethane over the glass-ceramic surface.

4. A method in accordance with claim 1 which comprises passing the gaseous stream through a cast alloy tube within which the gaseous stream is exposed to the glass-ceramic.

5. A method in accordance with claim 1 which comprises passing the gaseous stream over a glass-ceramic having a composition composed essentially of the oxides of barium, aluminum and silicon.

6. A method in accordance with claim 1 which comprises passing the gaseous stream over a glass-ceramic containing a predominant barium silicate crystal phase.

7. A method in accordance with claim 1 which comprises heating the tube to a temperature in the range of 750°–900° C. and passing the gaseous stream over the glass-ceramic surface.

8. A method in accordance with claim I which comprises the further step of providing a layer of a barium silicate glass-ceramic within the interior of the metal tube and exposing the gaseous stream to the surface of that layer.

9. A method in accordance with claim 1 which further comprises forming a solid body of a barium silicate glass-ceramic and inserting the solid body in a reactor tube to provide an exposure surface for the gaseous stream.

* * * * *